US012625148B2

(12) United States Patent
Kudo et al.

(10) Patent No.: US 12,625,148 B2
(45) Date of Patent: May 12, 2026

(54) METHOD FOR COLLECTING EXTRACELLULAR VESICLES DERIVED FROM NERVOUS SYSTEM CELLS

(71) Applicants: OSAKA UNIVERSITY, Suita-shi (JP); TOSOH CORPORATION, Shunan-shi (JP)

(72) Inventors: Takashi Kudo, Suita (JP); Kanta Yanagida, Suita-shi (JP); Shoshin Akamine, Suita-shi (JP)

(73) Assignees: OSAKA UNIVERSITY, Suita (JP); TOSOH CORPORATION, Shunan (JP)

( * ) Notice: Subject to any disclaimer, the term of this patent is extended or adjusted under 35 U.S.C. 154(b) by 947 days.

(21) Appl. No.: 17/757,939

(22) PCT Filed: Dec. 23, 2020

(86) PCT No.: PCT/JP2020/048209
§ 371 (c)(1),
(2) Date: Jun. 23, 2022

(87) PCT Pub. No.: WO2021/132352
PCT Pub. Date: Jul. 1, 2021

(65) Prior Publication Data
US 2023/0036973 A1 Feb. 2, 2023

(30) Foreign Application Priority Data

Dec. 27, 2019 (JP) ................................ 2019-239839

(51) Int. Cl.
| | |
|---|---|
| *G01N 33/68* | (2006.01) |
| *C12Q 1/6869* | (2018.01) |
| *C12Q 1/6883* | (2018.01) |
| *G01N 1/34* | (2006.01) |

(52) U.S. Cl.
CPC ....... *G01N 33/6896* (2013.01); *C12Q 1/6883* (2013.01); *G01N 1/34* (2013.01); *C12Q 1/6869* (2013.01); *C12Q 2600/158* (2013.01); *G01N 2333/4709* (2013.01); *G01N 2800/30* (2013.01)

(58) Field of Classification Search
CPC .. G01N 33/6896; G01N 1/34; G01N 2800/30; G01N 2800/2821; G01N 2333/4709; G01N 33/5076; G01N 33/5058; C12Q 1/6883; C12Q 1/6869; C12Q 2600/158; C12N 2506/45; C12N 5/0618; C12N 15/101; C12N 15/1013; C07K 16/28
See application file for complete search history.

(56) References Cited

U.S. PATENT DOCUMENTS

| | | |
|---|---|---|
| 5,851,787 A | 12/1998 | Wasco et al. |
| 2018/0066307 A1 | 3/2018 | Ter-Ovanesyan et al. |
| 2020/0309791 A1 | 10/2020 | Goetzl |
| 2022/0099686 A1 | 3/2022 | Moon |

FOREIGN PATENT DOCUMENTS

| | | |
|---|---|---|
| CN | 111323598 A | 6/2020 |
| JP | 2017167157 A | 9/2017 |
| JP | 2019516106 A | 6/2019 |
| WO | 2015061634 A2 | 4/2015 |
| WO | 2017193115 A1 | 11/2017 |
| WO | 2018094120 A1 | 5/2018 |
| WO | 2019144056 A1 | 7/2019 |
| WO | 2020111887 A1 | 6/2020 |

OTHER PUBLICATIONS

Canadian Office Action dated Mar. 19, 2025 for corresponding Canadian patent application No. 3, 165,950, 5 pages.
Extended European Search Report dated Feb. 3, 2023 for corresponding European Application No. 20908316.1, 7 pages.
Van Der Kant et al., "Cellular functions of the amyloid precursor protein from development to dementia", Developmental Cell, 2015, vol. 32, No. 4, pp. 502-515.
International Search Report dated Mar. 23, 2021 for International Application No. PCT/JP2020/048209, 5 pages with English translation.
Office Action dated May 15, 2025 for corresponding Chinese Application No. 202080095321.8 with machine English language translation, 13 pages.

*Primary Examiner* — Olga N Chernyshev
(74) *Attorney, Agent, or Firm* — MH2 Technology Law Group, LLP

(57) ABSTRACT

The present invention addresses a problem of providing a method for collecting extracellular vesicles derived from nervous system cells at an improved efficiency.
This problem is solved by a method for collecting extracellular vesicles derived from nervous system cells, said method comprising a step for mixing an anti-APLP1 antibody with a sample containing extracellular vesicles to form anti-APLP1 antibody-extracellular vesicle complexes and a step for collecting the anti-APLP1 antibody-extracellular vesicle complexes.

4 Claims, 2 Drawing Sheets

METHOD FOR COLLECTING EXTRACELLULAR VESICLES DERIVED FROM NERVOUS SYSTEM CELLS

CROSS-REFERENCE TO RELATED APPLICATIONS

This application is a U.S. National Stage application of PCT/JP2020/048209 filed 23 Dec. 2020, which claims priority to Japanese Application No. 2019-239839 filed 27 Dec. 2019, the entire disclosures of which are hereby incorporated by reference in their entireties.

TECHNICAL FIELD

The present description discloses a method for collecting extracellular vesicles derived from nervous system cells, a method for detecting a neuropsychiatric disorder, a method for collecting components derived from nervous system cells, a reagent for collecting extracellular vesicles, and a kit for detecting extracellular vesicles containing the reagent.

BACKGROUND ART

Patent Literature 1 discloses biomarkers and diagnostic and prognostic methods for Alzheimer's disease and other neurodegenerative disorders. Patent Literature 2 discloses that biomarkers in vesicles (for example, exosomes) isolated from a biological sample are detected to be used for diagnosis and prognostication of Alzheimer's disease and other neurodegenerative disorders. Patent Literature 3 discloses methods for quantifying subpopulations of exosomes and diagnostic and prognostic methods for neurodegenerative disorders (for example, Alzheimer's disease). Patent Literature 4 discloses how to use exosomes and exosomal biomarkers in diagnostic and prognostic methods for neurological disorders, immunological disorders, placental diseases, cancer, hematological disorders, kidney disease, gastrointestinal diseases, liver diseases, and musculoskeletal diseases.

CITATION LIST

Patent Literature

Patent Literature 1: WO2015/061634
Patent Literature 2: WO2017/193115
Patent Literature 3: WO2018/094120
Patent Literature 4: WO2019/144056

SUMMARY OF INVENTION

Technical Problem

Patent Literatures 2 to 4 disclose use of exosomes for diagnosis and prognostication of neurodegenerative disorders. However, for example, NCAM or CD171 used for collecting exosomes described in Patent Literature 2 is not a protein specific to nervous system cells. In order to efficiently collect extracellular vesicles derived from nervous system cells, it is necessary to collect extracellular vesicles derived from nervous system cells using a protein highly specific to other nerve cells. The present invention addresses a problem of providing a method for collecting extracellular vesicles derived from nervous system cells at an improved efficiency.

Solution to Problem

As a result of diligent research, the present inventors have found that extracellular vesicles derived from nervous system cells can be efficiently collected by performing immunoprecipitation targeting APLP1 present in the extracellular vesicles.

The present invention includes, for example, the following aspects as an embodiment.

Item 1. A method for collecting extracellular vesicles derived from nervous system cells comprising a step of mixing an anti-APLP1 antibody and a sample containing extracellular vesicles to form a complex of the anti-APLP1 antibody and the extracellular vesicle, and a step of collecting the complex of the anti-APLP1 antibody and the extracellular vesicle.

Item 2. The method for collecting the extracellular vesicles according to item 1, wherein the sample containing the extracellular vesicles contains the extracellular vesicles crudely purified from a specimen.

Item 3. The method for collecting the extracellular vesicles according to item 1 or 2, wherein the crude purification is performed by a size exclusion chromatography, an ultracentrifugation, an affinity purification, a polymer precipitation, or a combination thereof.

Item 4. A method for detecting the neuropsychiatric disorder comprising a step of obtaining measured values of polypeptides and/or polynucleotides that are a biomarker of the neuropsychiatric disorder from the extracellular vesicles collected by the method according to any one of claims 1 to 3, and a step of comparing the measured value with a corresponding reference value to determine whether the measured value is within or outside a reference range.

Item 5. The method for detecting the neuropsychiatric disorder according to item 4, wherein the neuropsychiatric disorder is selected from neurodegenerative disorder, post-cerebral spinal trauma neurologic dysfunction, brain tumor, infection-related cerebrospinal disorder, multiple sclerosis, schizophrenia, and bipolar disorder.

Item 6. The method for detecting the neuropsychiatric disorder according to item 5, wherein the neurodegenerative disorder is selected from dementia, Parkinson's disease, amyotrophic lateral sclerosis, progressive supranuclear palsy, multiple system atrophy, and triplet repeat disease.

Item 7. A method for collecting components derived from the nervous system cells comprising a step of collecting at least one biomolecule selected from the group consisting of sugar, lipid, polypeptide, and polynucleotide from the extracellular vesicles collected by the method according to any one of items 1 to 3.

Item 8-1. A test reagent used to collect the extracellular vesicles comprising an anti-APLP1 antibody.

Item 8-2. The test reagent according to item 8-1, wherein the extracellular vesicles are derived from nervous system cells.

Item 8-3. A test reagent comprising the anti-APLP1 antibody, wherein the test reagent is used to carry out the method for collecting the extracellular vesicles according to any one of items 1 to 3, carry out the method for detecting the neuropsychiatric disorder according to any one of items 4 to 6, or carry out the method for collecting the components derived from the nervous system cells according to item 7.

Item 9-1. A test kit comprising the test reagent comprising the anti-APLP1 antibody used to collect the extracellular vesicles.

Item 9-2. The test kit according to item 9-1 wherein the extracellular vesicles are derived from the nervous system cells.

Item 9-3. The test kit comprising the test reagent comprising an anti-APLP1 antibody wherein the test kit used to carry out the method for collecting the extracellular vesicles according to any one of items 1 to 3, carry out the method for detecting the neuropsychiatric disorder according to any one of items 4 to 6, or carry out the method for collecting the components derived from the nervous system cells according to item 7.

Advantageous Effects of Invention

According to the present invention, it is possible to provide an improved efficient method for collecting extracellular vesicles derived from nervous system cells.

DESCRIPTION OF EMBODIMENTS

1. Method for Collecting Extracellular Vesicles

Figure 1:
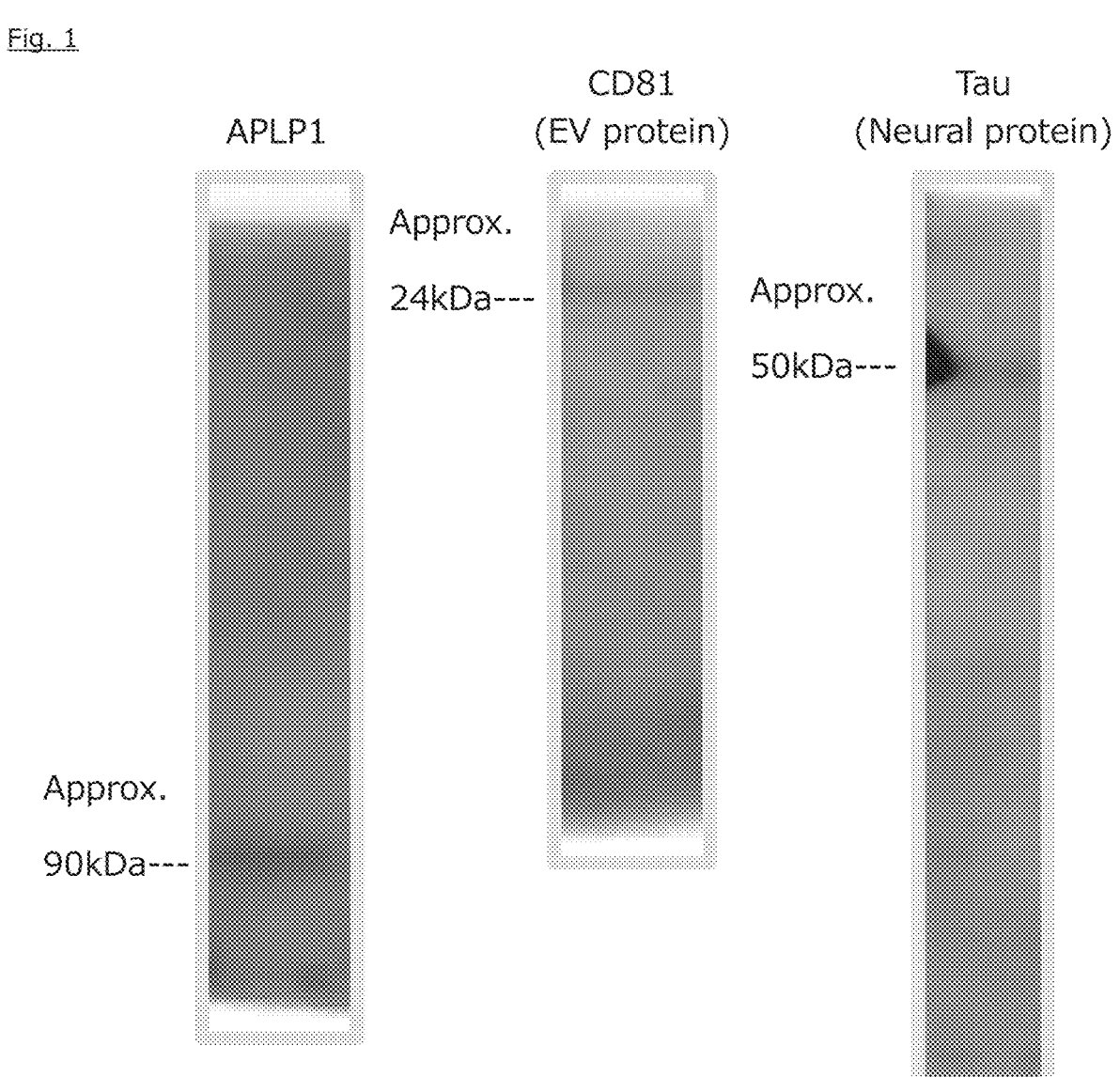
FIG. 1 shows results of Western Blot of extracellular vesicles collected from plasma.

This embodiment relates to a method for collecting extracellular vesicles derived from nervous system cells. The method for collecting extracellular vesicles comprises a step of mixing an anti-APLP1 antibody and a sample containing the extracellular vesicles, and a step of collecting a complex of the anti-APLP1 antibody and the extracellular vesicles. In the method for collecting the extracellular vesicles, the complex of the anti-APLP1 antibody and the extracellular vesicles can be formed by mixing the anti-APLP1 antibody and the sample containing the extracellular vesicles.

The extracellular vesicles are particles having a size of about several tens to several thousand nm and covered with a membrane containing phospholipids released from cells as a main component. The extracellular vesicles include exosomes, microvesicles, apoptotic bodies, and the like. Biomolecules are often present in the extracellular vesicles. For example, the exosome or the microvesicle comprises at least one biomolecule selected from the group consisting of polypeptides and polynucleotides (RNA such as mRNA, miRNA, and non-coding RNA, and DNA). For example, the apoptotic body includes at least one selected from the group consisting of fragmented nuclei and organelles. The extracellular vesicle preferably comprises at least one biomolecule selected from the group consisting of polypeptides and polynucleotides. More preferably, the extracellular vesicle comprises at least one biomolecule selected from the group consisting of polypeptides and polynucleotides. Here, the polypeptide refers to a compound in which a plurality of amino acids are bound by a peptide bond, and includes a protein having a relatively large molecular weight and a peptide having a relatively small molecular weight.

Amyloid beta precursor like protein 1: APLP1 is one of the members of the amyloid precursor protein gene family, and the APLP1 protein is expressed in a brain and is a membrane-bound glycoprotein cleaved by a secretase similar to the cleavage of amyloid beta A4 precursor protein. An intracellular cytoplasmic fragment that may act as a transcriptional activator is released by this cleavage. Human APLP1 is registered, for example, with Gene ID: 333. NCBI Reference Sequence is, for example, NM_001024807.3. Two variants have been reported for human APLP1, but in the present embodiment, the type of variant is not limited.

The nervous system cells can include nerve cells and glial cells. The glial cells can include astrocytes, oligodendrocytes and microglial cells.

The sample contains extracellular vesicles crudely purified from a specimen containing the extracellular vesicles. The sample may be a dispersion of extracellular vesicles or a pellet of the extracellular vesicles.

Methods for crudely purifying extracellular vesicles from a specimen are known, and for example, extracellular vesicles can be crudely purified by a size exclusion chromatography, an ultracentrifugation, an affinity purification, a polymer precipitation, or a combination thereof. Known methods can be used as these crude purification methods. The size exclusion chromatography is not limited as long as the extracellular vesicles can be fractionated by size. For example, the size exclusion chromatography can be performed using an extracellular vesicle isolation kit qEV (Izon Science) or the like. In the case of ultracentrifugation, extracellular vesicles can be obtained, for example, by ultracentrifuging at 100,000 g to 150,000 g for about 2 to 3 hours. Preferably, the specimen is preferably diluted with PBS, HEPES buffer, cell culture medium or the like so that the specific gravity becomes about 1.000 to 1.010 when performing ultracentrifugation, if necessary. The affinity purification may include, for example, a phosphatidylserine affinity purification, a CD63 affinity purification, an anion affinity purification, and the like. The polymer precipitation is a method of precipitating extracellular vesicles using a polyether such as a polyethylene glycol, a polypropylene glycol, or a polytetramethylene glycol. The crude purification of extracellular vesicles is preferably performed by a method capable of obtaining extracellular vesicles having a size of about 70 nm to 1000 nm.

The specimen is taken from a living body of an animal, preferably a mammal such as a human, a mouse, a rat, a rabbit, a dog, a cat, a cow, a pig, or a horse, and is not limited as long as it contains extracellular vesicles. For example, the specimen includes whole blood, serum, plasma, lymph, urine, ascites, pleural effusion, cerebrospinal fluid, intercellular fluid, tears, nasal discharge, saliva, and the like.

The anti-APLP1 antibody is not limited as long as it can bind at least a portion of the APLP1 protein. In addition, the anti-APLP1 antibody may be one type or a mixture of a plurality of types. As the "antibody", any of a polyclonal antibody, a monoclonal antibody, and a fragment thereof (for example, Fab, F(ab'), F(ab)$_2$, and the like) can be used. The class and subclass of immunoglobulin are not particularly limited. In addition, the antibody may be one screened from an antibody library, such as a chimeric antibody, scFv, or the like. For example, R&D SYSTEMS AF3129 can be used as the anti-APLP1 antibody.

The antibody does not necessarily have to be purified, and may be an antiserum containing the antibody, ascites, an immunoglobulin fraction fractionated from these, or the like.

In addition, the antibody may be bound to a carrier. Examples of the carrier include a known carrier used for immunoprecipitation. For example, the carrier is magnetic bead, agarose bead, cellulose bead, microplate, tube or the like.

Mixing the anti-APLP1 antibody and the sample containing the extracellular vesicles is not limited as long as the mixing is performed under conditions such that the anti-APLP1 antibody can bind to APLP1 present in the extracellular vesicles. As an example, Tris-HCl buffer, phosphoric acid buffer, HEPES buffer, maleic acid buffer, CHAPS buffer, and the like whose pH is about 6 to 9 can be included. It is preferable to add sodium chloride to these buffers in the same amount as saline. In addition, a bovine serum albumin, a skim milk or the like may be added as a blocking reagent. The reaction temperature is about 4° C. to 37° C. Furthermore, the reaction between the antibody and the extracellular vesicle is preferably carried out with stirring. The reaction time depends on the reaction temperature, but is about 4 hours to 48 hours when the reaction temperature is about 4° C., and about 0.5 hours to 4 hours when the reaction temperature is about 37° C.

By the above reaction, the anti-APLP1 antibody binds to the extracellular vesicle, and a complex of the anti-APLP1 antibody and the extracellular vesicle (also referred to as "anti-APLP1 antibody-extracellular vesicle complex") is formed.

Collecting the anti-APLP1 antibody-extracellular vesicle complexes can be performed by a known method. When the anti-APLP1 antibodies are bound to carriers in advance, the collecting method can be selected according to properties of the carrier. For example, when the carriers are magnetic beads, the anti-APLP1 antibody-extracellular vesicle complexes can be adsorbed on magnets and collected. When the carriers are non-magnetic beads such as agarose beads or cellulose beads, the anti-APLP1 antibody-extracellular vesicle complexes can be collected by centrifugation.

When the anti-APLP1 antibodies are not previously bound to carriers, carriers that are bound to substances having an affinity for the antibody used, for example, a secondary antibody that binds to the anti-APLP1 antibody, protein A or protein G, may be used to collect the anti-APLP1 antibody-extracellular vesicle complexes. The method for collecting the carriers and the anti-APLP1 antibody-extracellular vesicle complexes bound to the carriers is the same as when the anti-APLP1 antibodies are previously bound to the carriers.

In the process of collecting the anti-APLP1 antibody-extracellular vesicle complexes, a step of washing the anti-APLP1 antibody-extracellular vesicle complexes for B (bound)/F (free) separation in which the extracellular vesicles unreacted with the anti-APLP1 antibody and anti-APLP1 antibodies unreacted with the extracellular vesicles are appropriately removed may be included.

Since APLP1 is a protein specifically expressed in nervous system cells, extracellular vesicles derived from nervous system cells can be collected by the above collecting method.

2. Method for Detecting Neuropsychiatric Disorder

In this embodiment, the extracellular vesicles collected in the above 1 are used to detect neuropsychiatric disorder.

The method for detecting neuropsychiatric disorder includes a step of obtaining a measured value of the polypeptide and/or the polynucleotide of the biomarker of neuropsychiatric disorder from the extracellular vesicles collected in the above 1 and comparing the measured values with a corresponding reference value to determine whether the measured value is within or outside a reference range. When the measured value is outside the reference range, it can be determined that a subject from whom the specimen was taken suffers from the neuropsychiatric disorder. Alternatively, if the measured value is within the reference range, it can be determined that the subject from whom the specimen was taken dose not suffer from the neuropsychiatric disorder.

In addition, the severity of the neuropsychiatric disorder may be determined by determining how much the measured value is dissociated from the reference value.

The neuropsychiatric disorder can include psychiatric disorder and nervous system disease. The nervous system disease can include neurodegenerative disorder, post-cerebral spinal trauma neurologic dysfunction, brain tumor, infection-related cerebrospinal disorder, multiple sclerosis, and the like. The neurodegenerative disorder can include dementia, Parkinson's disease, amyotrophic lateral sclerosis, progressive supranuclear palsy, multiple system atrophy, triplet repeat disease, and the like. The dementia can include Alzheimer's disease, senile dementia, Lewy body disease, frontotemporal dementia, vascular dementia, alcohol-related dementia and corticobasal degeneration. The infection-related cerebrospinal disorder can include meningitis, brain abscess, Creutzfeldt-Jakob disease, and AIDS dementia. The brain tumor can include astrocytoma.

The psychiatric disorder can include schizophrenia, depression, bipolar disorder, and the like.

For example, a tau protein contained in an extracellular vesicle, particularly a phosphorylated tau protein, is a biomarker for Alzheimer's disease. When a measured value of the tau protein or the phosphorylated tau protein in a specimen taken from a subject is higher than a reference value, the subject can be determined to have Alzheimer's disease.

As biomarkers reported in each disease, α-synuclein for Parkinson's disease and dementia with Lewy body; TAR DNA-binding protein (TDP-43) for amyotrophic lateral sclerosis and frontotemporal dementia; abnormal prion protein for Creutzfeldt-Jakob disease; Neurofilament Light Chain for post-cerebral spinal trauma neurologic dysfunction, multiple sclerosis, amyotrophic lateral sclerosis, progressive supranuclear palsy, multiple system atrophy, triplet repeat disease, Alzheimer's disease, Lewy body disease, frontotemporal dementia, vascular dementia, corticobasal degeneration, and the like can be included. In addition, insulin-like growth factor (IGF-1) and brain-derived neurotrophic factor (BDNF) for depression; microRNA hsa-miR-34a, microRNA hsa-miR-432 for schizophrenia; IGF-1, BDNF, and the like for bipolar disorder can be included.

The biomarker for the neuropsychiatric disorder contained in an extracellular vesicle is detected as a polypeptide or as a polynucleotide. The polynucleotide may be RNA or DNA, and the RNA may include microRNA, ncRNA. and the like in addition to mRNA. The polypeptide and/or the polynucleotide of the biomarker for the neuropsychiatric disorder may include their fragment as well as full length one.

The method for detecting the biomarker for the neuropsychiatric disorder as a polypeptide may include known methods such as Western blotting, Enzyme-Linked Immuno Sorbent Assay (ELISA), and the like. In addition, the method for detecting the biomarker for the neuropsychiatric disorder as RNA may include known methods such as RT-PCR (including quantitative RT-PCR), microarray, RNA-Seq, and the like. The method for detecting the biomarker for the neuropsychiatric disorder as DNA may include known methods such as PCR (including quantitative PCR), microarray, sequencing, and the like.

When the biomarker for the neuropsychiatric disorder is detected as a polypeptide by Western blotting, ELISA or the like, extracellular vesicles are lysed with a predetermined lysis buffer as a pretreatment. A sample lysed with the lysis buffer is used as a test sample.

Primary antibody for detecting the biomarker of the neuropsychiatric disorder by Western blotting, ELISA, and the like, are not limited as long as the biomarker of the neuropsychiatric disorder can be detected.

When the biomarker for the neuropsychiatric disorder is detected as RNA by RT-PCR, microarray, RNA-Seq, and the like, the RNA is extracted from extracellular vesicles as a pretreatment. Further, if necessary, the extracted RNA may be used as a template for reverse transcription to synthesize complementary DNA (cDNA). RNA or cDNA can be used to detect the biomarker.

As a primer used for RT-PCR (in the case of quantitative RT-PCR, a probe may be included), a commercially available primer can be used. In addition, a commercially available microarray can also be used.

For the RNA-Seq, a next-generation sequencer (for example, manufactured by Illumina) or the like can be used to obtain the number of reads of mRNA of the biomarker for the neuropsychiatric disorder.

When the biomarker for the neuropsychiatric disorder is detected as DNA by PCR, microarray, sequencing, or the like, DNA is extracted from extracellular vesicles as a pretreatment. Further, if necessary, an amplification reaction may be carried out using the extracted DNA as a template. The DNA extracted from the extracellular vesicles or the amplified DNA can be used to detect the biomarker.

As a primer used for PCR (in the case of quantitative PCR, a probe may be included), a commercially available primer can be used. In addition, a commercially available microarray can also be used.

For the sequencing, the next-generation sequencer (for example, manufactured by Illumina) or the like can be used to obtain the number of reads of DNA associated with the biomarker for the neuropsychiatric disorder.

When the biomarker for the neuropsychiatric disorder is detected by Western blotting, ELISA, RT-PCR, PCR, RNA-Seq, sequencing, microarray, or the like, if the biomarker for the neuropsychiatric disorder is detected in extracellular vesicles, it may be determined that "the biomarker for the neuropsychiatric disorder is detected" or "an expression of the biomarker for the neuropsychiatric disorder is positive". Alternatively, when the amount of polypeptide of the biomarker for the neuropsychiatric disorder derived from extracellular vesicles of a subject and the amount of polypeptide of the biomarker for the neuropsychiatric disorder derived from extracellular vesicles of a healthy individual are compared, or the amount of polynucleotide of the biomarker for the neuropsychiatric disorder derived from the extracellular vesicles of the subject and the amount of polynucleotide of the biomarker for the neuropsychiatric disorder derived from the extracellular vesicles of the healthy individual are compared, if the amount of polypeptide of the biomarker for the neuropsychiatric disorder or the amount of polynucleotide of the biomarker for the neuropsychiatric disorder in the test sample taken from the subject is a higher value than the amount of polypeptide of the biomarker for the neuropsychiatric disorder or the amount of polynucleotide of the biomarker for the neuropsychiatric disorder in the extracellular vesicles taken from the healthy individual, it may be determined that "the biomarker for the neuropsychiatric disorder is detected" or "an expression of the biomarker for the neuropsychiatric disorder is positive". In addition, if the amount of polypeptide of the biomarker for the neuropsychiatric disorder or the amount of polynucleotide of the biomarker for the neuropsychiatric disorder in the extracellular vesicles taken from the subject is the same degree as the amount of polypeptide of the biomarker for the neuropsychiatric disorder or the amount of polynucleotide of the biomarker for the neuropsychiatric disorder in the extracellular vesicles taken from the healthy individual, it may be determined that "the biomarker for the neuropsychiatric disorder is not detected" or "an expression of the biomarker for the neuropsychiatric disorder is negative". Here, the expression "is a higher value" can be exemplified as a case where the value shows a value 1.2 times or more, preferably 1.5 times or more, more preferably 2 times or more, still more preferably 5 times or more. The expression "is the same degree" can be exemplified as a case where the value shows a value about 0.8 times to less than 1.2 times. In addition, before comparing the amounts of polypeptide of the biomarker for the neuropsychiatric disorder in a subject and that in a healthy individual or the amounts of polynucleotide of the biomarker for the neuropsychiatric disorder in the subject and that in the healthy individual, the number of extracellular vesicles purified from each specimen may be normalized by the amount of polypeptide of CD9, CD63, CD81, or the like that is a marker for the extracellular vesicle. Further, the normalization of the number of extracellular vesicles may be performed by the number of particles measured by Nanoparticle Tracking Analysis method or the like. The amount of the polypeptide may be expressed by mass or concentration, and may also be expressed by emission intensity of a substrate or the like. The amount of the polynucleotide may be the number of copies or the number of reads of the polynucleotide, and may be expressed by fluorescence intensity or the like.

As another embodiment, a reference value for the amount of polypeptide or RNA of the biomarker for the neuropsychiatric disorder is determined in advance, and if the amount of polypeptide or RNA of the biomarker for the neuropsychiatric disorder in the extracellular vesicles derived from the subject is out of a reference range, it may be determined that "the biomarker for the neuropsychiatric disorder is detected" or "an expression of the biomarker for the neuropsychiatric disorder is positive". In addition, if the amount of the polypeptide or the RNA of the biomarker for the neuropsychiatric disorder in the extracellular vesicles derived from the subject is within the reference range, it may be determined that "the biomarker of the neuropsychiatric disorder is not detected" or "the expression of the biomarker for the neuropsychiatric disorder is negative". The reference value is not limited as long as it is a value that can determine whether the amount of the polypeptide of the biomarker for the neuropsychiatric disorder or the amount of the polynucleotide of the biomarker for the neuropsychiatric disorder is detected or not or whether the expression of the biomarker for the neuropsychiatric disorder is positive or not, and can be determined by a known method. The value that can determine whether the amount of the polypeptide of the biomarker for the neuropsychiatric disorder or the amount of the polynucleotide of the biomarker for the neuropsychiatric disorder is detected or not or whether the expression of the biomarker for the neuropsychiatric disorder is positive or not can also be determined by an ROC (receiver operating characteristic curve) curve, a discriminant analysis method, a mode method, a Kittler method, a $3\sigma$ method, a p-tile method, or the like. Further, as a reference value, sensitivity, specificity, negative predictive value, positive predictive value, first quartile, and the like can be exemplified.

3. Method for Collecting Components Derived from Nervous System Cells

In this embodiment, the extracellular vesicles collected in the above 1 are used to collect the components derived from nervous system cells.

The method for collecting the components derived from the nervous system cells comprises a step of collecting at least one biomolecule selected from the group consisting of sugar, lipid, polypeptide, and polynucleotide from the extracellular vesicles collected in the above 1.

The sugar may include monosaccharide, disaccharide, oligosaccharide, and polysaccharide. In addition, the sugar may be bound to lipid, protein, or the like. Collecting sugar from the extracellular vesicles can be performed by a known method using a hydrazide/oxyamine-carrying polymer, a lectin, or the like.

The lipid may include fatty acid, eicosanoid, triacylglycerol, wax ester, phospholipid, sphingolipid, isoprenoid, lipoprotein, and the like. Extracting lipid from the extracellular vesicles can be performed by using Folch method, lipid extraction kit (Lipid Extraction Kit: Cell Biolabs, Inc.), or the like.

The polypeptide and polynucleotide may also contain the biomarker described in the above 2 and a component other than the above biomarker. The description of the biomarker is incorporated herein by reference.

The step of collecting polypeptides and polynucleotides can be performed according to known methods. In addition, a commercially available extraction kit may be used.

4. Test Reagent

In this section, the test reagent for collecting extracellular vesicles is described. The test reagent comprises at least an anti-APLP1 antibody. The description of the anti-APLP1 antibody is incorporated herein by reference to the description in the above 1.

The anti-APLP1 antibody comprised in the test reagent may be one kind or two or more kinds.

The anti-APLP1 antibody comprised in the test reagent may be in a dry state or may be dissolved in a buffer such as phosphate-buffered saline. Further, the test reagent may comprise at least one of a stabilizer such as beta-mercaptoethanol and DTT; a protective agent such as albumin; a surfactant such as polyoxyethylene (20) sorbitan monolaurate and polyoxyethylene (10) octylphenyl ether; a preservative such as sodium azide, and the like.

The anti-APLP1 antibody may be labeled with an enzyme or a fluorescent dye. The antibody that binds to adipophilin may be immobilized on a microplate, magnetic beads, or the like.

5. Test Kit

In this section, the kit comprising the test reagent for collecting extracellular vesicles described in the above 4 is described.

The test kit may be provided as a test kit that includes a package insert that describes the test reagent and how to use the reagent or that describes a URL of a web page that describes how to use the reagent. In addition, when the anti-APLP1 antibody dose not bind to a carrier or a solid phase, secondary antibody-conjugated beads, Protein A beads, Protein G beads, a secondary antibody immobilized microplate, a Protein A-immobilized microplate, a Protein G-immobilized microplate, a secondary antibody-immobilized tube, and the like for binding the anti-APLP1 antibody to the carrier or the solid phase may be comprised.

Further, the test kit may comprise a column for size exclusion chromatography, a column for affinity purification, a polyether such as polyethylene glycol, and the like for crudely purifying the extracellular vesicles.

Furthermore, it may comprise an antibody, a probe, a primer, or the like for detecting the biomarker of the neuropsychiatric disorder present in the extracellular vesicles.

EXAMPLES

Hereinafter, the present embodiment will be described in more detail with reference to Examples, but the present invention is not construed as being limited to the Examples.

1. Example 1: Collecting Nervous System Cells-Derived Extracellular Vesicles from Plasma by Using Anti-APLP1 Antibody (i) Specimen Blood was collected from a patient using an EDTA-2K tube, and 20 mL of plasma was separated. The plasma was stored at −80° C. until testing. At the time of use, the plasma was thawed and centrifuged at 2,500 g, 4° C. for 10 minutes, and supernatant was collected.

(ii) Crude Purification of Extracellular Vesicles in Plasma 20 mL of size exclusion chromatography (SEC) fraction was collected from 10 mL of the plasma by using qEV10 (Meiwafosis Co., Ltd.) according to a protocol attached to it. The above step was carried out twice in total, and 40 mL of the SEC fraction was collected. The SEC fraction was concentrated to 600 µL by using Amicon Ultra-15 100 kDa MWCO.

(iii) Preparation of Beads for Immunoprecipitation 5 mg of DYNABEADS® (magnetic beads) M-270 Epoxy of DYNABEADS® Antibody Coupling Kit (Thermo Fisher Scientific) and 10 µg of anti-APLP1 antibody (R&D SYSTEMS AF3129) were coupled according to a protocol attached to the kit to prepare magnetic beads to which the anti-APLP1 antibody was bound.

(iv) Immunoprecipitation of Extracellular Vesicles Derived from Nervous System Cells 100 µL of the beads for immunoprecipitation prepared in the above (iii) was added to 600 µL of the concentrated SEC fraction in a tube, and incubated at 4° C. for 4 hours while being inverted and mixed. After spinning down the tube, it was attached to a magnetic stand and waited for 1 minute and then, remove the supernatant. Subsequently, in order to wash the magnetic beads, 800 µL of D-PBS (−) was added to the tube and mixed by inversing. After spinning down the tube, it was attached to the magnetic stand and waited for 1 minute and then, remove the supernatant. It was spun down again, attached to the magnetic stand, waited for 1 minute and then the supernatant was completely removed.

The tube with magnetic beads remained in it was added with 17 µL of 2× Laemmli Buffer, and after vortexing, incubated at 97° C. for 5 minutes. After spinning down the tube, it was attached to the magnetic stand and waited for 1 minute and the supernatant was collected and then used for analysis.

(5) Western Blot

The supernatant collected in the previous step was mixed with denaturing buffer and then heated to prepare a sample for application. The sample was loaded into a 5-15% Tris-glycine SDS gel and run at 200 V for 55 minutes. The SDS gel after electrophoresis was run under semi-dry conditions at 15 V for 30 minutes using Towbin Buffer (with 5% methanol) to perform transfer from the gel to a PVDF membrane.

Blocking was performed at room temperature for 1 hour using 2% ECL Prime Blocking Agent dissolved in TBS-T. Primary antibodies were diluted with 2% ECL Prime Blocking Agent dissolved in TBS-T and reacted at 4° C. overnight. The antibodies used were anti-APLP1 antibody (Calbiochem, 171615), anti-CD81 antibody (Santa Cruz, sc-23962), and anti-Tau antibody (Merck Millipore, 5778801), and all of them were diluted 1,000 times to be used. After reacting with the primary antibodies, a 5-minute wash was performed 6 times using TBS-T.

The secondary antibody was diluted with 2% ECL Prime Blocking Agent dissolved in TBS-T and reacted at room temperature for 1 hour. The antibodies used were HRP-labeled anti-mouse antibody (Promega, W4021) and HRP-labeled anti-rabbit antibody (Promega, W4011), all of them were diluted 10,000 times to be used. A 5-minute wash was performed 6 times using TBS-T.

1,400 μL of ImmunoStar® LD A+B solution was added to the membrane, and the mixture was reacted at room temperature for 5 minutes. By using myECL Imager (Thermo Scientific), HRP was emitted and the signal was imaged.

(6) Results

The results of Western Blot are shown in FIG. 1.

In addition to the targeted APLP1, CD81 that is an extracellular vesicle (EV) protein and Tau that is a neural protein were detected by immunoprecipitation using plasma. From this, it was found that APLP1-positive EV could be isolated and neural proteins exist in it, and consequently, extracellular vesicles derived from nervous system cells could be collected.

2. Example 2: Extracellular Vesicles from Culture Supernatant of Nerve Cells Differentiated from iPS Cells (i) Preparation of Beads for Immunoprecipitation 5 mg of DYNABEADS® (magnetic beads) M-270 Epoxy of DYNABEADS® Antibody Coupling Kit (Thermo Fisher Scientific) and 10 μg of anti-APLP1 antibody (R&D SYSTEMS AF3129) were coupled according to a protocol attached to the kit to prepare magnetic beads to which the anti-APLP1 antibody was bound.

(ii) Preparation of Extracellular Vesicles (EV) in the Culture Supernatant

The culture supernatant of the nerve cells differentiated from iPS cells was centrifuged at 2,500 g for 10 minutes, and the supernatant was put in 4 ultracentrifugation tubes by 12 mL each. After ultracentrifugation at 120,000 g for 2.5 hours, the supernatant was removed and pellet containing extracellular vesicles was collected. The pellet was added with 12 mL of PBS, pipetted, and again ultracentrifuged at 120,000 g for 2.5 hours to collect the pellet. The pellet was added with 25 μL PBS, pipetted, and transferred to one 1.5 mL tube.

(iii) Immunoprecipitation and Western Blot

100 μL of DYNABEADS® (magnetic beads) coupled with APLP1 antibody was put in a screw cap tube. 20 μL of EV prepared by ultracentrifugation, 80 μL of ×10 complete (Roche), and 600 μL of PBS were added, and the mixture was incubated at 4° C. for 4 hours while being rotated and mixed. The tube was spun down, attached to a magnetic stand, and allowed to stand for 1 minute. The supernatant was transferred to another tube, 800 μL of PBS was added to the beads, and the tube was shaken up and down. The tube was spun down, attached to the magnetic stand, and allowed to stand for 1 minute. After removing the supernatant, 12 μL of ×2 sample buffer for Western blotting was added to the tube containing the beads, and the mixture was heated at 97° C. for 5 minutes after vortex. After centrifugation, it was attached to the magnetic stand and allowed to stand for 1 minute, and 10 μL was electrophoresed on a 5-20% or 15% SDS-PAGE gel. 20 μL of the supernatant after immunoprecipitation was taken in another tube, 4 μL×6 sample buffer was added, and the mixture was heated at 97° C. for 5 minutes after vortex. After centrifugation, 20 μL was electrophoresed on a 5-20% or 15% SDS-PAGE gel at a voltage of 120 V for 100 minutes.

The gel after electrophoresis was transferred to a PVDF membrane by wet transfer (400 mA, 1 hour). The membrane after blotting was blocked with 2% ECL Prime Blocking Reagent for 2 hours.

Subsequently, the membranes were added with APLP1 C-terminal antibody (Calbiochem 171615) diluted 10,000 times, L1CAM antibody (Santa Cruz sc-53386) diluted 1,000 times, CD63 antibody (Santa Cruz sc-5275) diluted 2,000 times, Flotillin-1 antibody (BD Transduction 610820) diluted 1,000 times and SNAP25 antibody (abcam ab5666) diluted 1,000 times with 2% ECL Prime Blocking Reagent respectively, and incubated overnight at 4° C. with shaking. After incubation, the membranes were washed with 0.1% TBS-T for 5 minutes 6 times.

The membranes reacted with L1CAM, CD63, and Flotillin-1 respectively were added with anti-Mouse IgG-HRP (Promega W402B) diluted 10,000 times with 2% ECL Prime Blocking Reagent as a secondary antibody and incubated at room temperature for 1 hour with shaking. The membranes reacted with APLP1 and SNAP25 respectively were added with anti-Rabbit IgG-HRP (Promega W401B) diluted 10,000 times with 2% ECL Prime Blocking Reagent as a secondary antibody and incubated at room temperature for 1 hour with shaking. After incubation, the membranes were washed with 0.1% TBS-T for 5 minutes 6 times.

Solution A and solution B of ImmunoStar® LD (Wako) were mixed in an amount of 800 μL each, and the membranes were immersed and allowed to stand for 5 minutes. A signal was detected by myECL Imager (Thermo Fisher Scientific) (10 to 300 seconds).

(iv) Results

Figure 2:
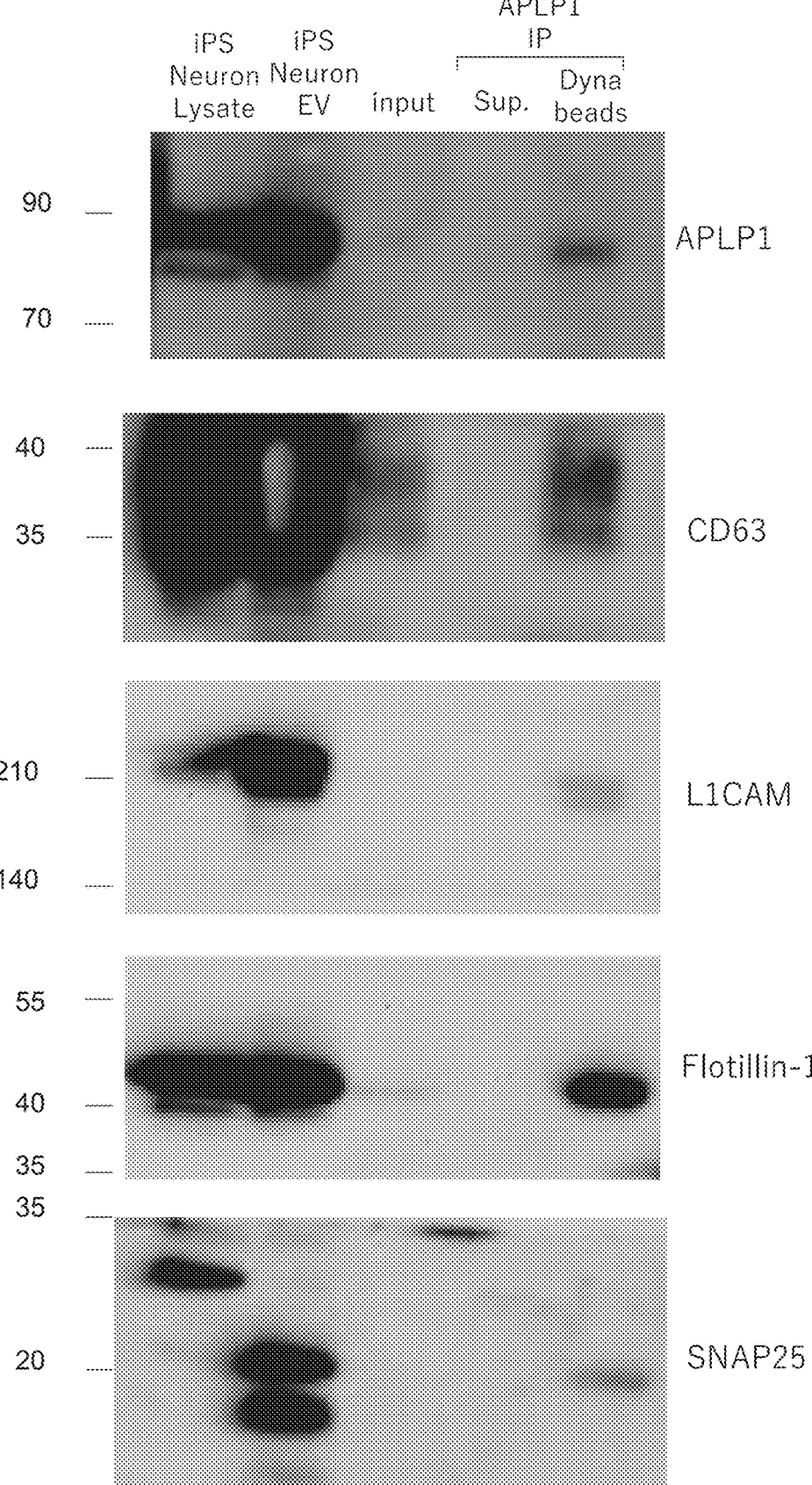
FIG. 2 shows results of Western Blot of extracellular vesicles collected from culture supernatant of nerve cells differentiated from iPS cells.

The results of Western Blot are shown in FIG. 2.

Lane 1 is 1 μg of iPS neuron lysate, lane 2 is EV before immunoprecipitation, lane 3 is input, lane 4 is the supernatant after immunoprecipitation of EV, and lane 5 is antibody-coupled beads after immunoprecipitation of EV. The amounts of the input and the supernatant electrophoresed were one-fortieth of the whole.

APLP1, EV marker protein (CD63, Flotillin-1), and nerve-derived protein (L1CAM, SNAP25) were detected in antibody beads. From this, it was found that extracellular vesicles can be collected by using the anti-APLP1 antibody.

The invention claimed is:

1. A method for collecting extracellular vesicles derived from nervous system cells comprising:

mixing an anti-amyloid beta precursor like protein 1 (anti-APLP1) antibody and a sample containing extracellular vesicles derived from nervous system cells to form a complex of the anti-APLP1 antibody and the extracellular vesicle, and collecting the complex of the anti-APLP1 antibody and the extracellular vesicle, thereby collecting the extracellular vesicles derived from the nervous system cells.

2. The method for collecting the extracellular vesicles according to claim 1, wherein the sample is obtained by crudely purifying the extracellular vesicles from a specimen containing the extracellular vesicles derived from nervous system cells before mixing the anti-APLP1 antibody and the sample.

3. The method for collecting the extracellular vesicles according to claim 2, wherein the extracellular vesicles are crudely purified from the specimen by a size exclusion chromatography, an ultracentrifugation, an affinity purification, a polymer precipitation, or a combination thereof.

4. The method according to claim 1, wherein the sample is obtained from a specimen selected from the group consisting of whole blood, serum, plasma, lymph, urine, ascites, pleural effusion, cerebrospinal fluid, intercellular fluid, tears, nasal discharge, and saliva, and the specimen contains the extracellular vesicles derived from the nervous system cells.

*     *     *     *     *